(12) United States Patent
Chen et al.

(10) Patent No.: US 10,370,651 B2
(45) Date of Patent: Aug. 6, 2019

(54) TARGET ANTIGEN DISCOVERY, PHENOTYPIC SCREENS AND USE THEREOF FOR IDENTIFICATION OF TARGET CELL SPECIFIC TARGET EPITOPES

(71) Applicant: X-BODY, INC., Waltham, MA (US)

(72) Inventors: Yan Chen, Lexington, MA (US);
Steven M. Shamah, Waltham, MA (US)

(73) Assignee: X-BODY, INC., Waltham, MA (US)

( * ) Notice: Subject to any disclaimer, the term of this patent is extended or adjusted under 35 U.S.C. 154(b) by 162 days.

(21) Appl. No.: 14/897,892

(22) PCT Filed: Jun. 20, 2014

(86) PCT No.: PCT/US2014/043454
§ 371 (c)(1),
(2) Date: Dec. 11, 2015

(87) PCT Pub. No.: WO2014/209801
PCT Pub. Date: Dec. 31, 2014

(65) Prior Publication Data
US 2016/0122747 A1    May 5, 2016

Related U.S. Application Data

(60) Provisional application No. 61/840,583, filed on Jun. 28, 2013.

(51) Int. Cl.
*C40B 30/04* (2006.01)
*C12N 15/10* (2006.01)
*G01N 33/68* (2006.01)

(52) U.S. Cl.
CPC ..... *C12N 15/1037* (2013.01); *G01N 33/6878* (2013.01); *C40B 30/04* (2013.01); *G01N 2500/04* (2013.01)

(58) Field of Classification Search
None
See application file for complete search history.

(56) References Cited

U.S. PATENT DOCUMENTS 6,794,128 B2   9/2004   Marks et al.
7,587,281 B2   9/2009   Gershoni et al.
(Continued)

FOREIGN PATENT DOCUMENTS

CN   1763082 A   4/2006
CN   1777684 A   5/2006
(Continued)

OTHER PUBLICATIONS

Bowley et al. (Jan. 12, 2009) PNAS USA vol. 106 pp. 1380 to 1385 and supporting information.*
(Continued)

*Primary Examiner* — Christian C Boesen
(74) *Attorney, Agent, or Firm* — Lathrop Gage LLP; James H. Velema, Esq.

(57) ABSTRACT

The invention provides methods and compositions for identifying binding polypeptides (e.g., antibodies or antigen binding fragments thereof) that specifically binds to a cell-surface antigen. The methods of the invention generally comprise contacting a variegated nucleic acid-display library of binding polypeptides with a cell-surface antigen displayed on the exterior surface of a cell; and isolating from the library at least one library member that specifically binds to the cell-surface antigen on the exterior surface of the cell.

13 Claims, 10 Drawing Sheets
Specification includes a Sequence Listing.

V_H Stripping from Cells by Restriction Digestion

(56) References Cited

U.S. PATENT DOCUMENTS

| | | | |
|---|---|---|---|
| 8,450,464 | B2 | 5/2013 | Kuhne et al. |
| 8,916,504 | B2 | 12/2014 | Hsieh et al. |
| 9,102,732 | B2 | 8/2015 | Lee et al. |
| 9,266,953 | B2 | 2/2016 | Finney et al. |
| 9,880,160 | B2 | 1/2018 | Chen et al. |
| 10,054,598 | B2 | 8/2018 | Steyaert et al. |
| 2004/0209261 | A1 | 10/2004 | Keys et al. |
| 2005/0255552 | A1 | 11/2005 | Flynn et al. |
| 2011/0076752 | A1* | 3/2011 | Wu ................. C07K 16/00 435/272 |
| 2011/0183863 | A1* | 7/2011 | Wagner .......... G01N 33/5308 506/9 |
| 2012/0288878 | A1 | 11/2012 | Urech et al. |

FOREIGN PATENT DOCUMENTS

| | | |
|---|---|---|
| EP | 2348052 A2 | 7/2011 |
| JP | 2012504415 A | 2/2012 |
| JP | 2013507980 A | 3/2013 |
| RU | 2346004 C2 | 2/2009 |
| WO | 1998/016541 A1 | 4/1998 |
| WO | 2007/047578 A2 | 4/2007 |
| WO | 2008/070367 A2 | 6/2008 |
| WO | 2010/011944 A2 | 1/2010 |
| WO | 2010/094027 A1 | 8/2010 |
| WO | 2012/007594 A1 | 1/2012 |
| WO | 2012/125733 A2 | 9/2012 |
| WO | 2012/162267 A2 | 11/2012 |
| WO | 2013/080055 A2 | 6/2013 |

OTHER PUBLICATIONS

Elortza et al. (2006) Journal of Proteome Research vol. 5 pp. 935 to 943.*

International Search Report with Written Opinion corresponding to International Patent Application No. PCT/US2014/043454, dated Oct. 13, 2014.

Cao et al. (Dec. 31, 2012) "Screening and Identification of Polypeptides Specifically Binding to Hepatoma Carcinoma Cells," Journal of Animal and Veterinary Advances. 11(12):2166-2175.

Doi et al. (Jan. 10, 2012) "DNA Display Selection of Peptide Ligands for a Full-Length Human G Protein-Coupled Receptor on CHO-K1 Cells," PLoS One. 7(1):e30084. pp. 1-8.

Pan et al. (Mar. 7, 2013) "肺癌特异性结合多肽的体外筛选和鉴定 [Screening and identifying the peptide specifically binding to lung cancer by using phage display in vitro]," 中国药理学通报 [Chinese Pharmacological Bulletin]. 29 (3)342-346—English Abstract Only.

Nishina et al. (Jan. 26, 2007) "Immunodetection of glycophosphatidylinositol-anchored proteins following treatment with phospholipase C," Analytical Biochemistry, pp. 318-320, vol. 363.

Poul (May 25, 2009) Antibody Phage Display pp. 155-163.

International Search Report with Written Opinion corresponding to International Patent Application No. PCT/US2014/056782, dated Jan. 7, 2015.

Becker et al. (2004) "Ultra-high-throughput screening based on cell-surface display and fluorescence-activated cell sorting for the identification of novel biocatalysts," Current Opinion in Biotechnology. 15(4):323-329.

Bowers et al. (2011) "Coupling mammalian cell surface display with somatic hypermutation for the discovery and maturation of human antibodies," Proc. Natl. Acad. Sci. USA. 108(51):20455-20460.

Wittrup (2001) "Protein engineering by cell-surface display," Current Opinion in Biotechnology. 12:395-399.

U.S. Appl. No. 15/024,002, filed Mar. 22, 2016, Yan Chen, 2016/0244743, Aug. 25, 2016.

* cited by examiner

These clones enrich through 4 rounds of selection and predict binding selectivity to Cell Type A

TARGET ANTIGEN DISCOVERY, PHENOTYPIC SCREENS AND USE THEREOF FOR IDENTIFICATION OF TARGET CELL SPECIFIC TARGET EPITOPES

RELATED APPLICATIONS

This application is a 35 U.S.C. § 371 filing of International Application No. PCT/US2014/043454, filed Jun. 20, 2014, which claims priority to related to U.S. Provisional Application No. 61/840,583, filed Jun. 28, 2013, entitled "Target Antigen Discovery and Phenotypic Screens", the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 9, 2017, is named 576943_XBI-010US_ST25.txt and is 2.36 kilobytes in size.

BACKGROUND

Binding polypeptides, such as antibodies and fragments thereof, are commercially important as therapeutic and diagnostic agents. Traditional methods of screening for binding polypeptide generally employ soluble antigens. However, for certain cell-surface antigens, conformational epitopes on these antigens are altered when the antigens are solubilized from the plasma membrane, resulting in a failure to generate binding polypeptides that can recognize the native antigen. Accordingly, there is a need in the art for novel methods of screening for binding polypeptides that can specifically bind to cell-surface antigens in their native conformation.

SUMMARY

The invention provides methods and compositions for identifying binding polypeptides (e.g., antibodies or antigen binding fragments thereof) that specifically binds to a cell-surface antigen. The methods of the invention generally comprise contacting a variegated nucleic acid-display library of binding polypeptides with a cell-surface antigen displayed on the exterior surface of a cell; and isolating from the library at least one library member that specifically binds to the cell-surface antigen on the exterior surface of the cell. The methods and compositions of the invention are particularly advantageous in that they allow for the rapid identification of binding polypeptides that bind to native forms of the target cell surface antigen. These methods and compositions also allow for identification of novel, therapeutically useful cell-type specific antigens or epitopes.

DETAILED DESCRIPTION

I. Definitions

Figure 1:
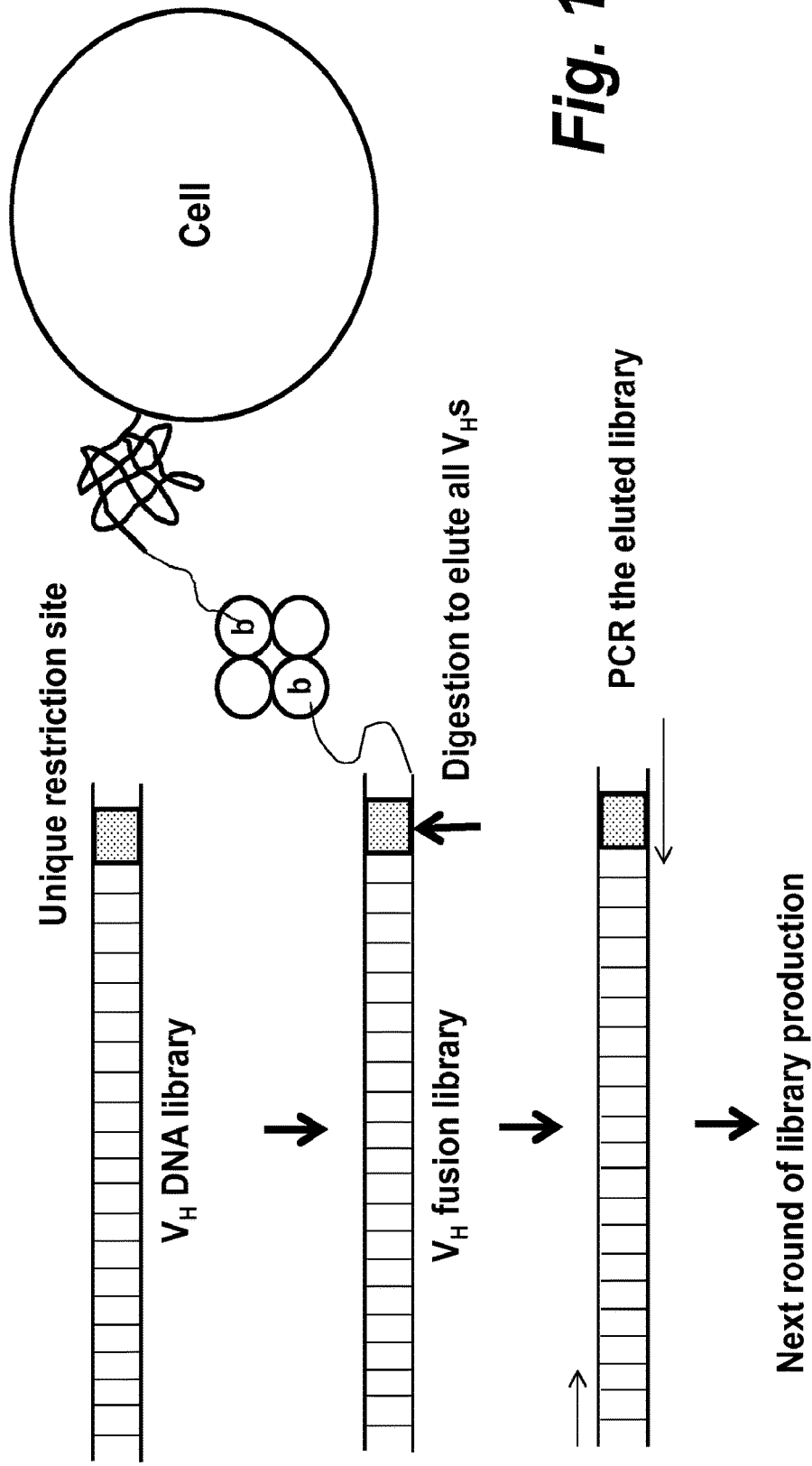
FIG. 1 is a schematic of exemplary DNA display compositions and screening methods of the invention.

As used herein, the term "nucleic acid display library" refers to any art recognized in vitro cell-free phenotype-genotype linked display, including, without limitation those set forth in, for example, U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315, and in WO2010/011944, which are all hereby incorporated by reference in their entirety.

As used herein, the term "antigen" refers to the molecule recognized by a binding polypeptide.

As used herein, the term "specifically binds to" refers to the ability of a binding molecule (e.g., a VH or VL domain) to bind to an antigen with an affinity of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or more, and/or bind to a target with an affinity that is at least two-fold greater than its affinity for a nonspecific antigen.

As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR).

As used herein, the term "antigen-binding portion" of an antibody includes any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding portion."

As used herein, the terms "VH domain" and "VL domain" refer to single antibody variable heavy and light domains, respectively, comprising FR (Framework Regions) 1, 2, 3 and 4 and CDR (Complementary Determinant Regions) 1, 2 and 3 (see Kabat et al. (1991) Sequences of Proteins of Immunological Interest. (NIH Publication No. 91-3242, Bethesda).

II. Cell Surface Antigens

In certain aspects, the invention provides methods of identifying a binding polypeptide that specifically binds to a cell-surface antigen.

Any antigen that is capable of being displayed on the surface of a cell can be employed in the methods of the invention, including without limitation, protein, glycan, and/or lipid antigens. In certain embodiments, the antigen is a naturally occurring molecule. Suitable, non-limiting examples of naturally occurring antigens include transmembrane proteins (e.g., G-protein coupled receptors) and GPI-anchored proteins. In certain embodiments, the antigen is a non-naturally occurring recombinant or synthetic antigen. Suitable, non-limiting examples of naturally occurring antigens include chimeric antigens comprising portions from different antigen molecules. In certain embodiments, the identity of the antigen is known prior to preforming the methods of the invention. In certain embodiments, the identity of the antigen is unknown prior to preforming the methods of the invention.

The cell surface antigens employed in the methods of the invention can be displayed on any cell or cell-like particle (e.g., lipid vesicle). In certain embodiments, the cell is a cell type that naturally expresses the cell-surface antigen. In certain embodiments, the cell is a recombinant cell that is engineered to heterologously express the cell-surface antigen. In certain embodiments, the cell is a disease-associated variant of a normal cell (e,g, a tumor cell).

III. Binding Polypeptides

In certain aspects, the invention provides methods of identifying a binding polypeptide that specifically binds to a cell-surface antigen.

Any type of binding polypeptide can be employed in the methods of the invention including, without limitation antibodies, or fragments thereof, and immunoglobulin-like domains. Suitable immunoglobulin-like domains include, without limitation, fibronectin domains (see, for example, Koide et al. (2007), *Methods Mol. Biol.* 352: 95-109, which is incorporated by reference herein in its entirety), DARPin (see, for example, Stumpp et al. (2008) *Drug Discov. Today* 13 (15-16): 695-701, which is incorporated by reference herein in its entirety), Z domains of protein A (see, Nygren et al. (2008) *FEBS J.* 275 (11): 2668-76, which is incorporated by reference herein in its entirety), Lipocalins (see, for example, Skerra et al. (2008) *FEBS J.* 275 (11): 2677-83, which is incorporated by reference herein in its entirety), Affilins (see, for example, Ebersbach et al. (2007) *J. Mol. Biol.* 372 (1): 172-85, which is incorporated by reference herein in its entirety), Affitins (see, for example, Krehenbrink et al. (2008). *J. Mol. Biol.* 383 (5): 1058-68, which is incorporated by reference herein in its entirety), Avimers (see, for example, Silverman et al. (2005) *Nat. Biotechnol.* 23 (12): 1556-61, which is incorporated by reference herein in its entirety), Fynomers, (see, for example, Grabulovski et al. (2007) *J Biol Chem* 282 (5): 3196-3204, which is incorporated by reference herein in its entirety), and Kunitz domain peptides (see, for example, Nixon et al. (2006) *Curr Opin Drug Discov Devel* 9 (2): 261-8, which is incorporated by reference herein in its entirety). In certain embodiments, the binding polypeptide is antibody VH or VL domain.

IV. Cell Surface Display Methods

In certain aspects, the invention provides a method of identifying a binding polypeptide that specifically binds to a cell-surface antigen, the method comprising: (a) contacting a variegated nucleic acid-display library of binding polypeptides with a cell-surface antigen displayed on the exterior surface of a first cell type; and (b) isolating from the library at least one library member that specifically binds to the cell-surface antigen on the exterior surface of the first cell type, thereby identifying a binding polypeptide that specifically binds to the cell surface antigen. In certain embodiments, prior to step (a), the variegated nucleic acid-display library of binding polypeptides is contacted with a second cell type that does not display the antigen displayed on the exterior surface, in order to pre-clear the library of binding polypeptides that do not specifically bind to the antigen.

In certain aspects, the invention provides a method of identifying a binding polypeptide that specifically binds to a cell-surface antigen, the method comprising: (a) contacting a variegated nucleic acid-display library of binding polypeptides with a first cell type expressing a cell-surface antigen, and isolating from the library at least one library member that specifically binds to the first cell type; (b) contacting the variegated nucleic acid-display library of binding polypeptides with a second cell type that does not express the cell surface antigen, and isolating from the library at least one library member that specifically binds to the second cell type; and (c) selecting library members that specifically bind to the first cell type but not to the second cell type, thereby identifying a binding polypeptide that specifically binds to the cell surface antigen.

Suitable nucleic acid-display libraries for use in the methods of the invention are set forth in, for example, U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315, and in WO2010/011944, which are all hereby incorporated by reference in their entirety. In certain embodiments, the variegated nucleic acid-display library is a DNA display library. In one embodiment, the nucleic acid-display library is a DNA display library described herein or in WO2010/011944, which is hereby incorporated by reference in its entirety.

In certain embodiments, each member of the DNA-display library comprises a binding polypeptide linked through an intervening DNA linker to a DNA coding sequence encoding the binding polypeptide, wherein the DNA linker comprising a restriction endonuclease site (see e.g., FIG. 1). Any restriction endonuclease site can be employed. In one particular embodiment, the restriction endonuclease site is not present in the DNA coding sequence of members of the DNA-display library, thus avoiding cleavage of the DNA coding sequence upon restriction endonuclease digestion of the library members. In one particular embodiment, the restriction endonuclease site is a NotI site.

In certain embodiments, it is desirable to physically separate the DNA coding sequence of the isolated library members from the linked binding polypeptide. Any methods of physical separation can be employed. Where the isolated library members comprise a DNA linker comprising a restriction endonuclease site (see e.g., FIG. 1), the physical separation can be achieved by restriction endonuclease digestion of the isolated library members. The resultant liberated DNA coding sequences can be further separated from the cell/binding polypeptide complexes by any art recognized method, e.g., centrifugation.

In certain embodiments, it is desirable to physically separate the intact isolated library members from the from the first and/or second cell type. Any methods of physical separation can be employed. In certain embodiments, the isolated library members are separated from the first or second cell type by enzymatic cleavage of the cell-surface antigen. Any methods of enzymatic cleavage of the antigen can be employed, e.g., protease, lipid, and/or glycosidase enzymatic cleavage. In certain embodiments, where the cell-surface antigen is attached to the cell surface by a glycolipid anchor, the isolated library members are separated from the first or second cell type by phospholipase cleavage of the glycolipid anchor. The resultant liberated isolated library members can be further separated from the first or second cell type by any art recognized method, e.g., centrifugation.

Once the library members that specifically bind to the first and/or second cell type have been isolated, the DNA coding sequence of these molecules can be determined. Accordingly, in certain embodiments, the methods of the invention further comprise the step of determining the DNA coding sequence of at least a portion of the isolated library members. Any art recognized means for DNA sequence determination can be employed. In one particular embodiment, the DNA coding sequence is determined by single molecule, deep sequencing techniques (e.g., pyrosequencing). Single molecule, deep sequencing techniques are well known in the art (see e.g., those described in U.S. Pat. No. 6,210,891, which is hereby incorporated by reference in its entirety). In certain embodiments, where the binding polypeptides are antibodies, or antigen binding fragments thereof, the DNA coding sequence of the CDR3 region is determined. In certain embodiments, the DNA coding sequences of the library member that bind to the first and second cell types are determined Library members that specifically bind to the first cell type but not to the second cell type are considered to comprise binding polypeptides that specifically bind to an antigen specific for the first cell type.

Once a binding polypeptide that specifically binds to the cell-surface antigen has been identified, it can be heterologously expressed in vitro (e.g., in cells or in a cell-free expression system) or in vivo (e.g., in a transgenic animal). Accordingly, in certain embodiments, the methods of the invention further comprise the step of heterologously expressing in vitro (e.g., in cells or in a cell-free expression system) or in vivo (e.g., in a transgenic animal), the identified binding polypeptide.

In certain embodiments, the identity of the antigen is known prior to preforming the methods of the invention. However, it is not necessary to know the identity of the antigen. Indeed, in certain embodiments, the identity of the antigen is unknown prior to preforming the methods of the invention. Thus, in this latter case, the methods of the invention allow for the identification of novel antigens and epitopes present on the surface of a cell type of interest (e.g., a tumor cell).

In certain embodiments, the methods disclosed herein comprise the selection of binding polypeptides that are capable of functional internalization upon binding to the cell surface antigen. Such binding polypeptides are particularly useful in the production of drug conjugates because they allow for the delivery of a cytotoxic drug to the interior of a target cell. Any methodology for screening for functional internalization can be employed. For example, the variegated nucleic acid-display library of binding polypeptides can be contacted with target cells under conditions that to allow for binding polypeptide internalization (e.g., for about 1-2 hours at 37° C.). The cells can then washed and lysed with cell lysis buffer in the presence of protease inhibitors. The internalized library members can then be ethanol precipitated and the DNA coding sequences enriched by PCR amplification.

The methods disclosed herein can be applied to any target epitope discovery process. For example, target epitopes can include: homing domains for inflammation; tumor specific target epitopes from primary tumors with or without resistance to treatment, tumor cell lines, and tumors that harbor any mutations that may result in neoepitopes; and other disease specific epitopes that mediate disease specific malfunction and be targeted for biologic therapy The methods disclosed herein can also be applied for biomarker discovery to monitor the presence or absence of particular cell surface epitopes over a course of a drug treatment to patients. The antibodies derived from the biomarker discovery can also be used as tools for biomarker detection.

Additionally or alternatively, the methods disclosed herein can be applied to target or epitope discovery in other species, such as in transgenic animals and animal disease models.

V. Exemplification

A. Summary

Figure 4:
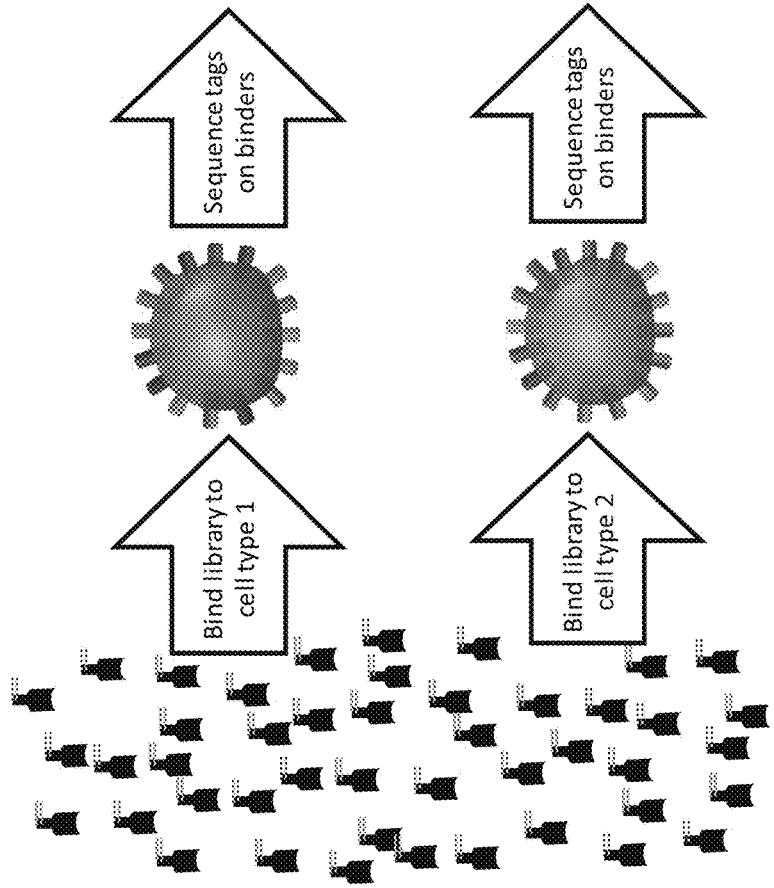
FIG. 4 is a schematic of exemplary parallel screening and deep sequencing strategies employed in the methods of the invention.
Figure 5:
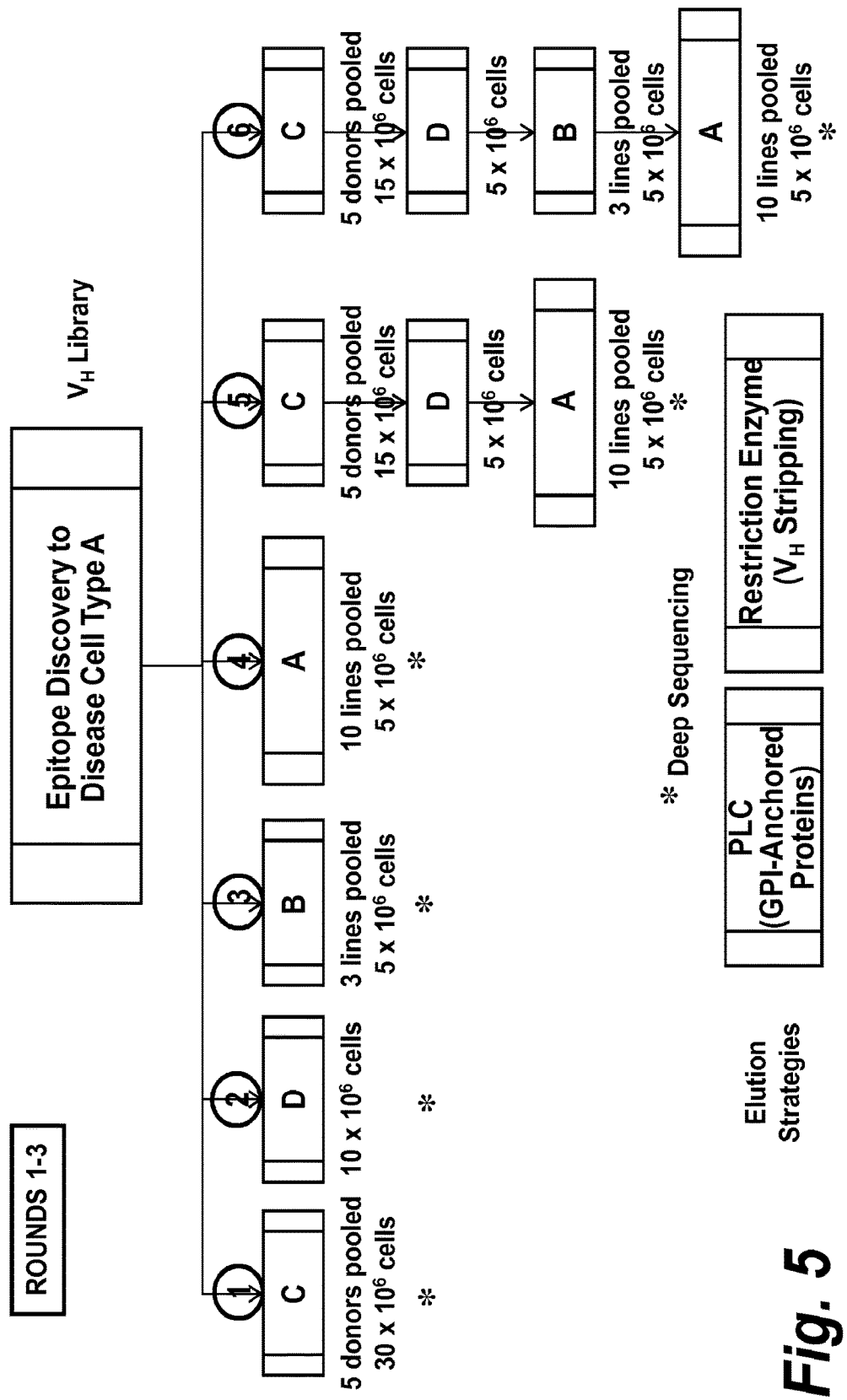
FIG. 5 is a schematic of exemplary parallel screening and deep sequencing strategies employed in the methods of the invention.
Figure 6:
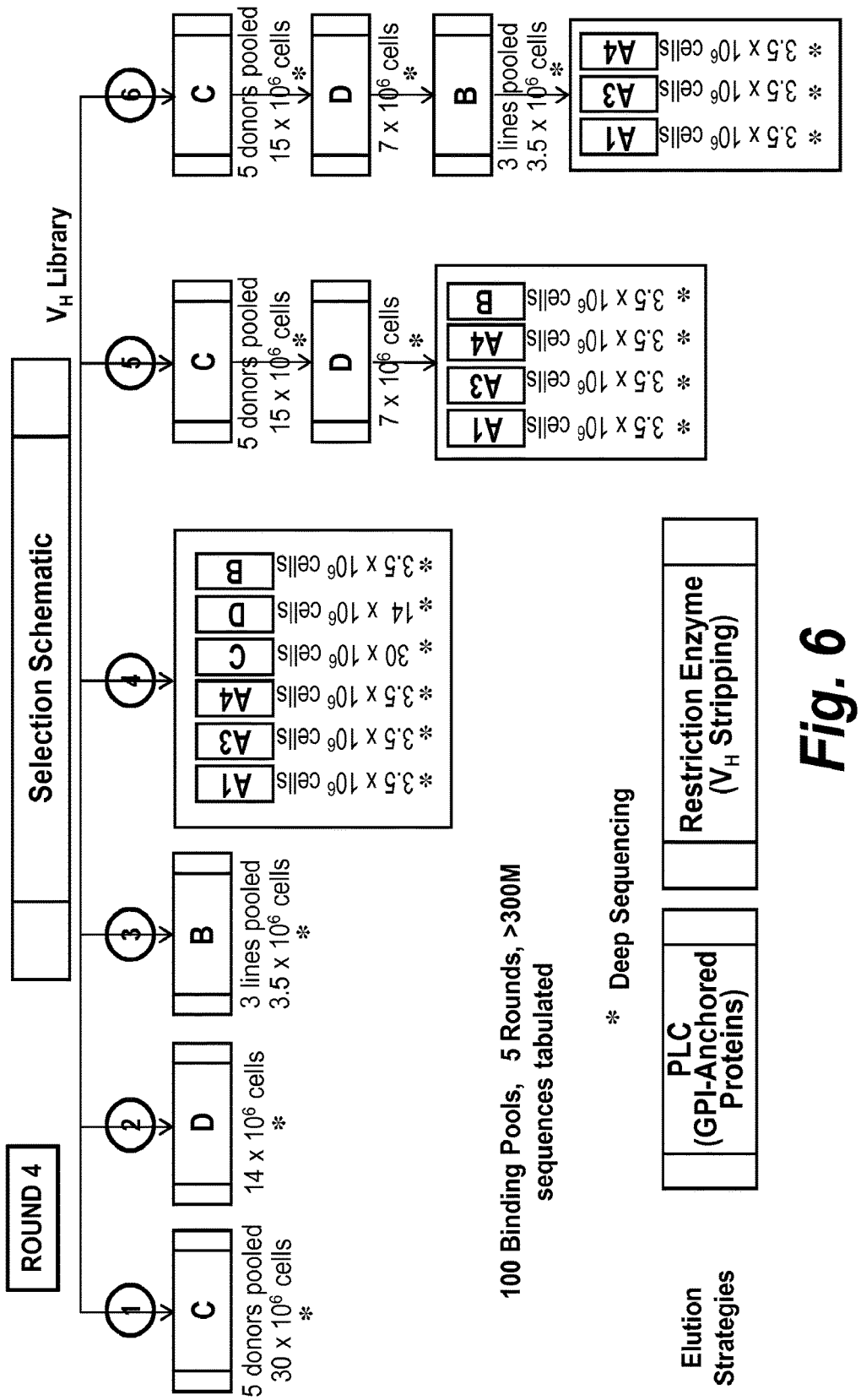
FIG. 6 is a schematic of exemplary parallel screening and deep sequencing strategies employed in the methods of the invention.

A fully human antibody VH library obtained from bone marrow, peripheral blood and splenocytes of human donors was constructed and numerous high affinity and specific VH binders to multiple targets were identified using dsDNA display technology. Target cell specific epitopes were identified by live cell selection and deep sequencing analysis using human VH library and dsDNA display technology. Strategies of parallel, differential selections and target cell selective selections were applied in these methods (see FIGS. 4, 5, 6). The tabulation of the CDR3 frequency from deep sequencing of all pools across all rounds predicted the selectivity of the VH clones. High affinity VHs were identified that selectively bind to target cells and related cell types.

B. Library Engineering and Selection Methods for Live Cell Epitope Discovery

Two methods were developed to effectively recover library members that bound to live cells.

The first method involved stripping off binders from live cells by restriction digestion of the DNA fused to bound antibodies. This method enables the full recovery of the VHs bound to all epitopes on cells. A C-terminal of VH DNA library was engineered to carry a NotI restriction site (see FIG. 1). There are no NotI sites in naïve VH frameworks and therefore only full length VH binders are eluted from cells for subsequent amplification. The NotI restriction digestion buffer was tested on live cells, and with up to a 2 hour incubation at 37 C the cells were viable. The efficiency of the NotI digestion was high. Following the binding of the library to cells for 1 hour at 4 C, the cells were washed and digested with NotI buffer at 37 C for 1 hour, the cells were then spun down, supernatant (containing bound VH DNA) was collected for PCR amplification (see FIG. 1).

Figure 2:
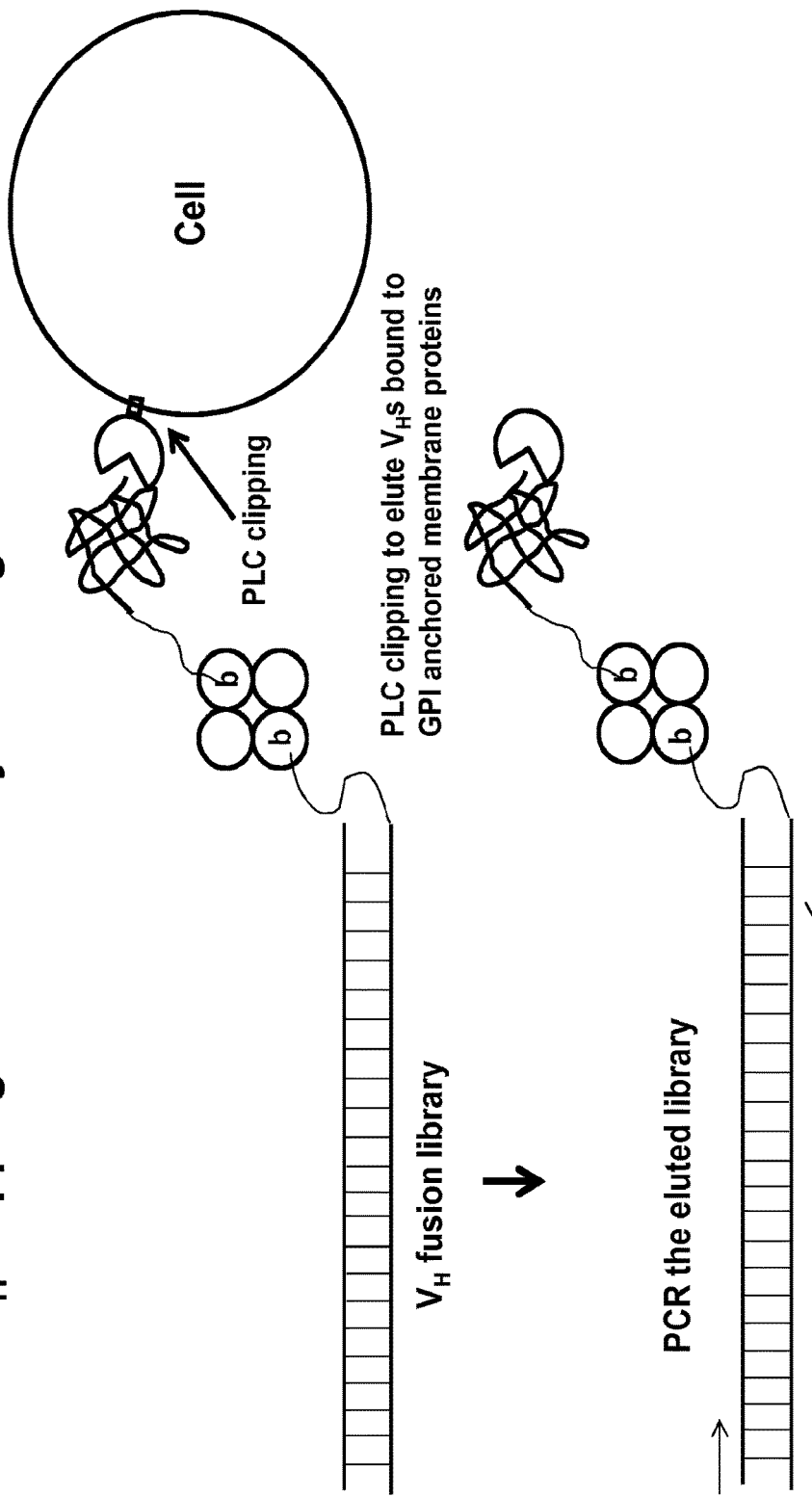
FIG. 2 is a schematic of exemplary DNA display compositions and screening methods of the invention.
Figure 3:
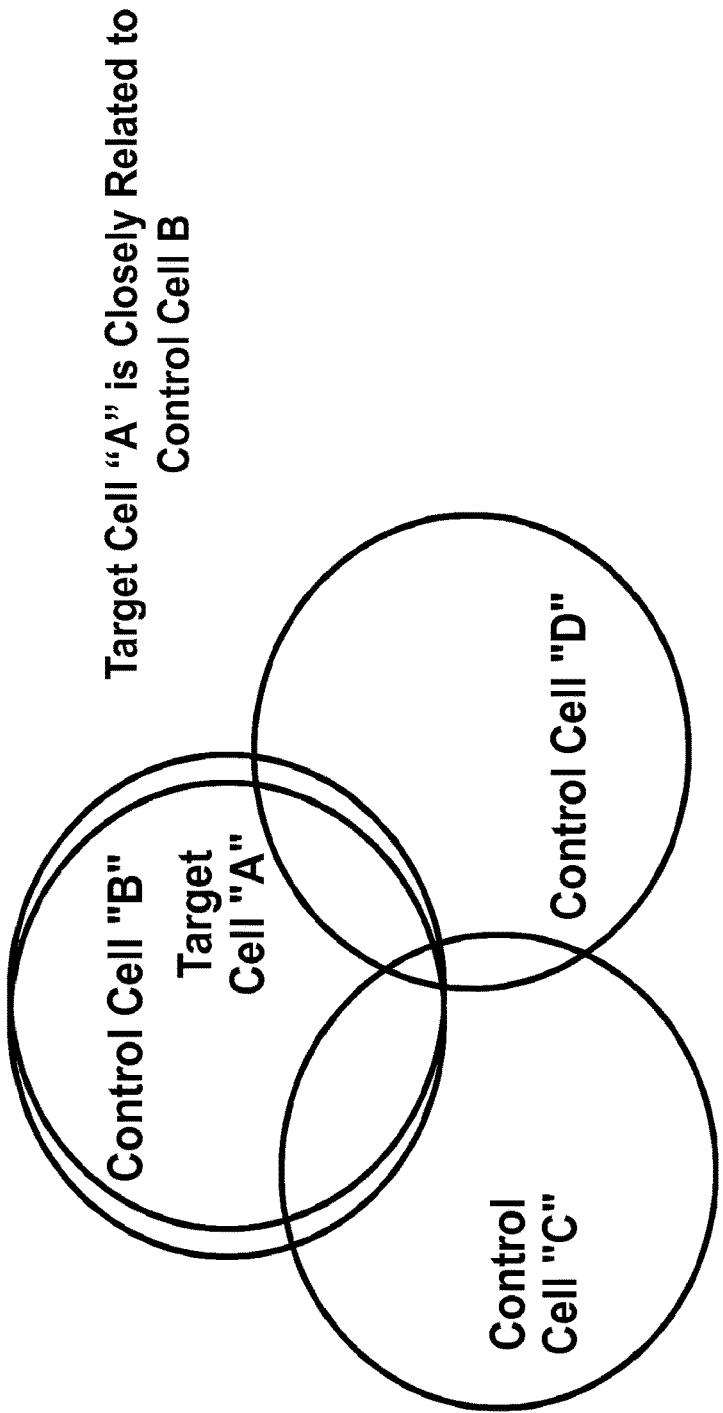
FIG. 3 is a schematic of exemplary target cell screening strategies employed in the methods of the invention.

The second method is to clip off VH binders from live cells using phospholipase C (PLC) digestion. This method enables the elution of the VHs that bound to the epitopes of any GPI anchored membrane protein (i.e., a subset of epitopes). The PLC clipping efficiency is high, as validated on FACS with control molecule. After incubation of library with cells for 1 hour at 4 C, the cells were washed and incubated with PLC at 37 C for 15 mins. The cells were subsequently spun down and the supernatant, containing fusion VH complexed with extracellular domain of the GPI anchored membrane protein, was PCR amplified (see FIG. 2).

C. Parallel Selections, Differential Selections and Target Cell Selective Selections on Target and Related/Undesired Cell Types Master naïve fusion library was produced according to the protocol set forth in WO2010/011944 (which is hereby incorporated by reference in its entirety). For first round of selection, the purified fusion library was split equally into multiple libraries that carry the same diversity for all selection branches (see FIG. 5).

Primary cells, obtained from normal donors or patients, were either thawed fresh or isolated from cell culture flasks, following standard cell biology protocols. The cells were then recovered for 1 hour in full media at 37 C followed by blocking in selection buffer for 30 mins on ice. All the selections were carried out on ice to prevent antibody and target internalization.

For parallel selections, libraries were pre-cleared with 200 ul of pre-blocked streptavidin beads and 200 ul of pre-blocked hIgG-Epoxy beads for 30 mins at room temperature sequencially to remove any misfold and sticky library members. The pre-cleared libraries were then chilled on ice and subjected to pre-blocked cells and incubated on ice for 1 hour.

For target cell selective selections, pre-clearance was performed on undesired and closely related cell types for 1 hour on ice to remove any non-selective binders and then subjected on target cells.

At selection round 4, differential selection methods were applied to the branches of selection on target cells (with and without pre-clearance on cells). In this round, libraries were split into multiple tubes and bound to each cell type and patient's cells from different stage of the diseases in parallel. This strategy allowed for direct comparison of target cells versus other cell types by deep sequencing analysis and identification of binders recognizing different epitopes that arose with disease progression (see FIG. 6).

For all selection branches, after binding, cells were washed with 10 mL of binding buffer and subject to either NotI restriction digestion to recover all binders to membrane protein or PLC clipping to recover binders to GPI anchored membrane proteins as described above.

D. Deep Sequencing Analysis to Predict Selective Binders to Target Cells

After each round of selection, binding pools were PCR amplified. The HCDR3 of each binding pool was lifted up by PCR with oligos priming C-terminal of framework 3 and N-terminal of framework 4 of VH fragments. These HCDR3 fragments derived from individual selection rounds and branches were then tagged with specific DNA bar code used for Illumina sequencing by PCR. The tagged HCDR3 were pooled and sent for high throughput sequencing with Hi Seq technology. The round 4 binding pools from target cells were also tagged with DNA bar code and submitted for 454 sequencing to get full length VH sequences.

Figure 7:
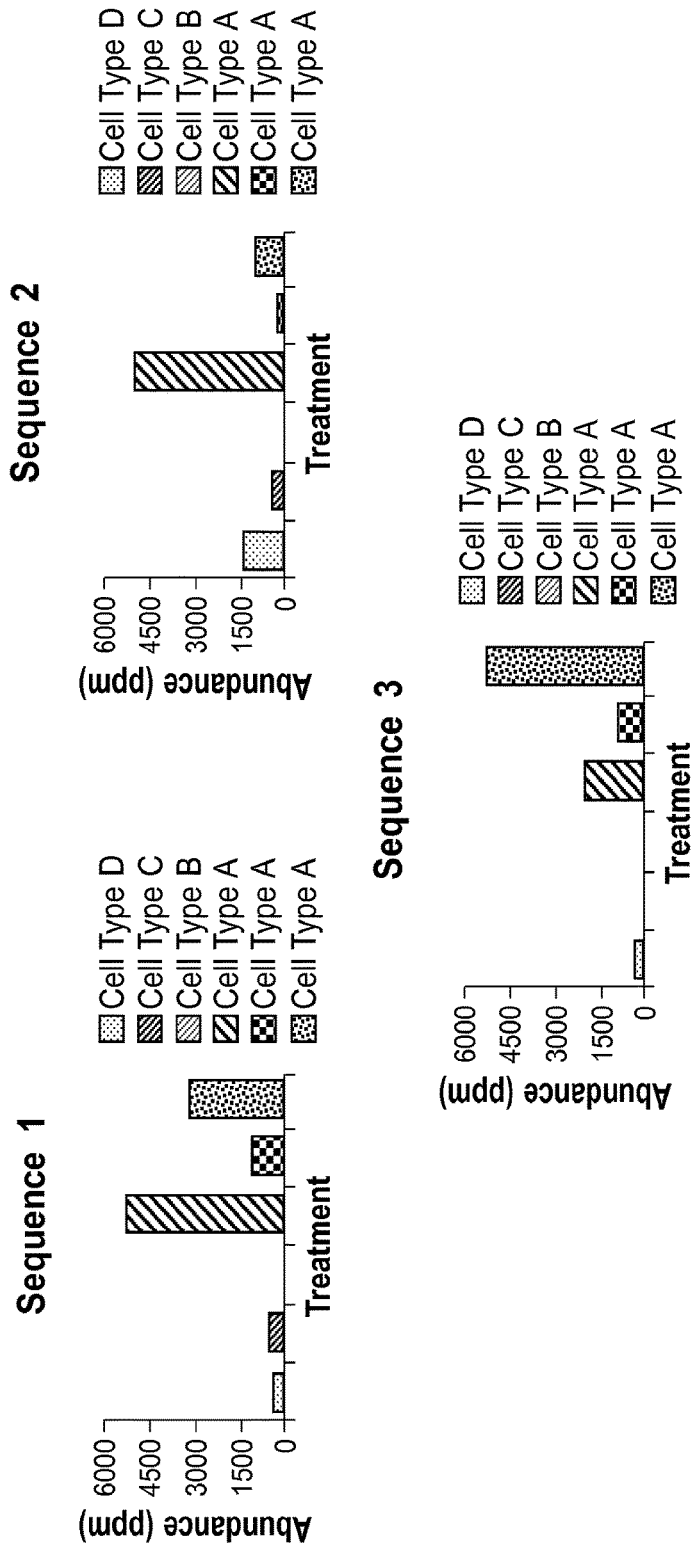
FIG. 7 is a schematic of the results of exemplary parallel screening strategies employed in the methods of the invention.

The sequences were deconvoluted based on the DNA bar code after sequencing. Millions of sequences derived from each selection round and selection branch were tabulated by comparing the frequency of a particular CDR3 sequence present at different rounds and selection branches. The criteria used for identification of selective binders were: 1) specific enrichment of a CDR3 sequence from earlier round to later round on target cells, not on control or close related cell types; 2) higher frequency on target specific cell type and low on control or closely related cell type at differential selection round (see FIG. 7); and 3) sequences not present in other target or cell selections from other programs in database. The selective clones identified by Illumina sequencing were then synthesized based on the 454 full length sequence information.

E. Production, Purification and FACS Binding Assays

Figure 8:
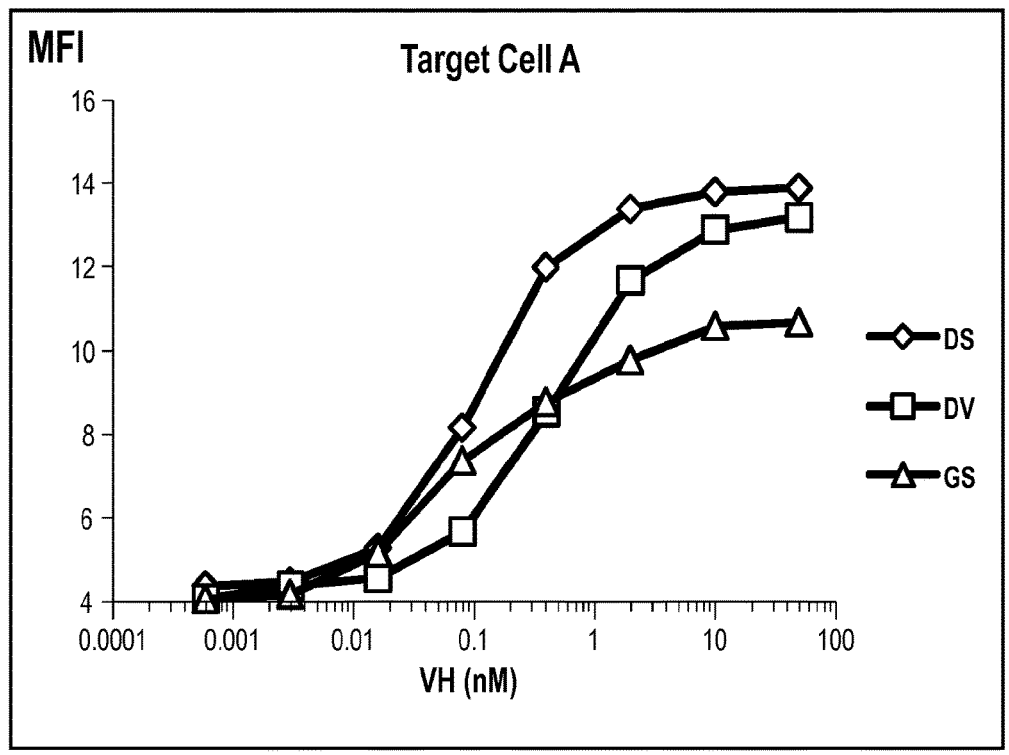
FIG. 8 depicts a graph showing the results of a FACS based binding assay of high affinity VH molecules selected using the methods of the invention.
Figure 9:
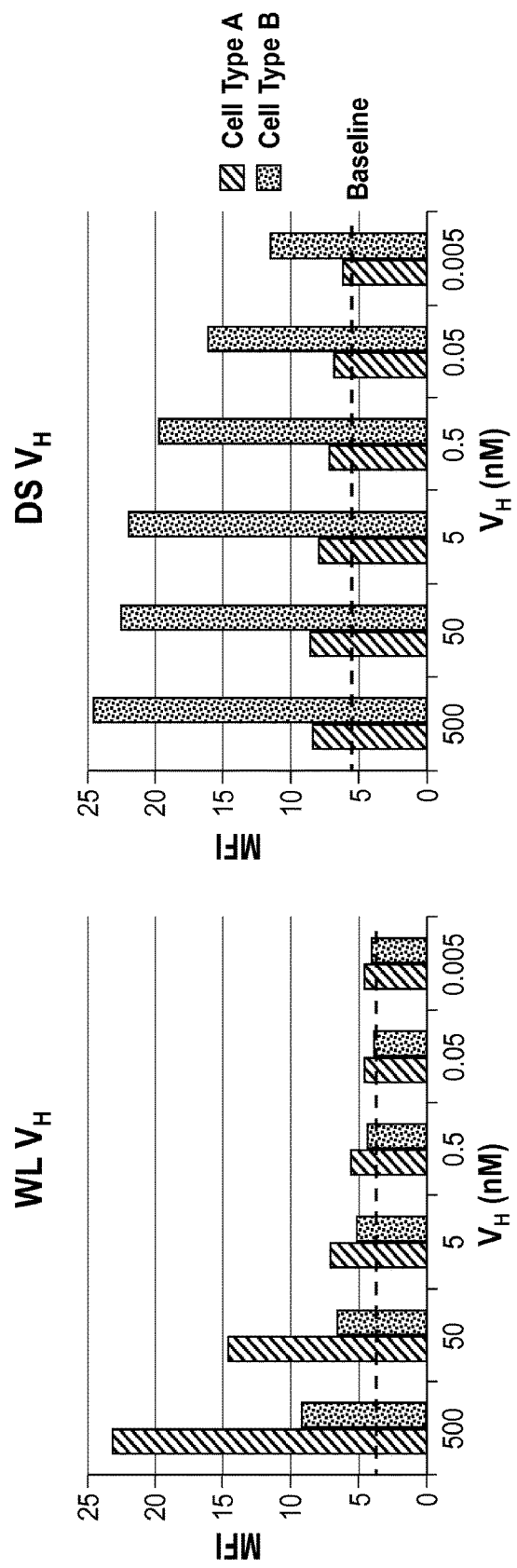
FIG. 9 depicts graphs showing the differential binding of VH molecules selected using the methods of the invention.
Figure 10:
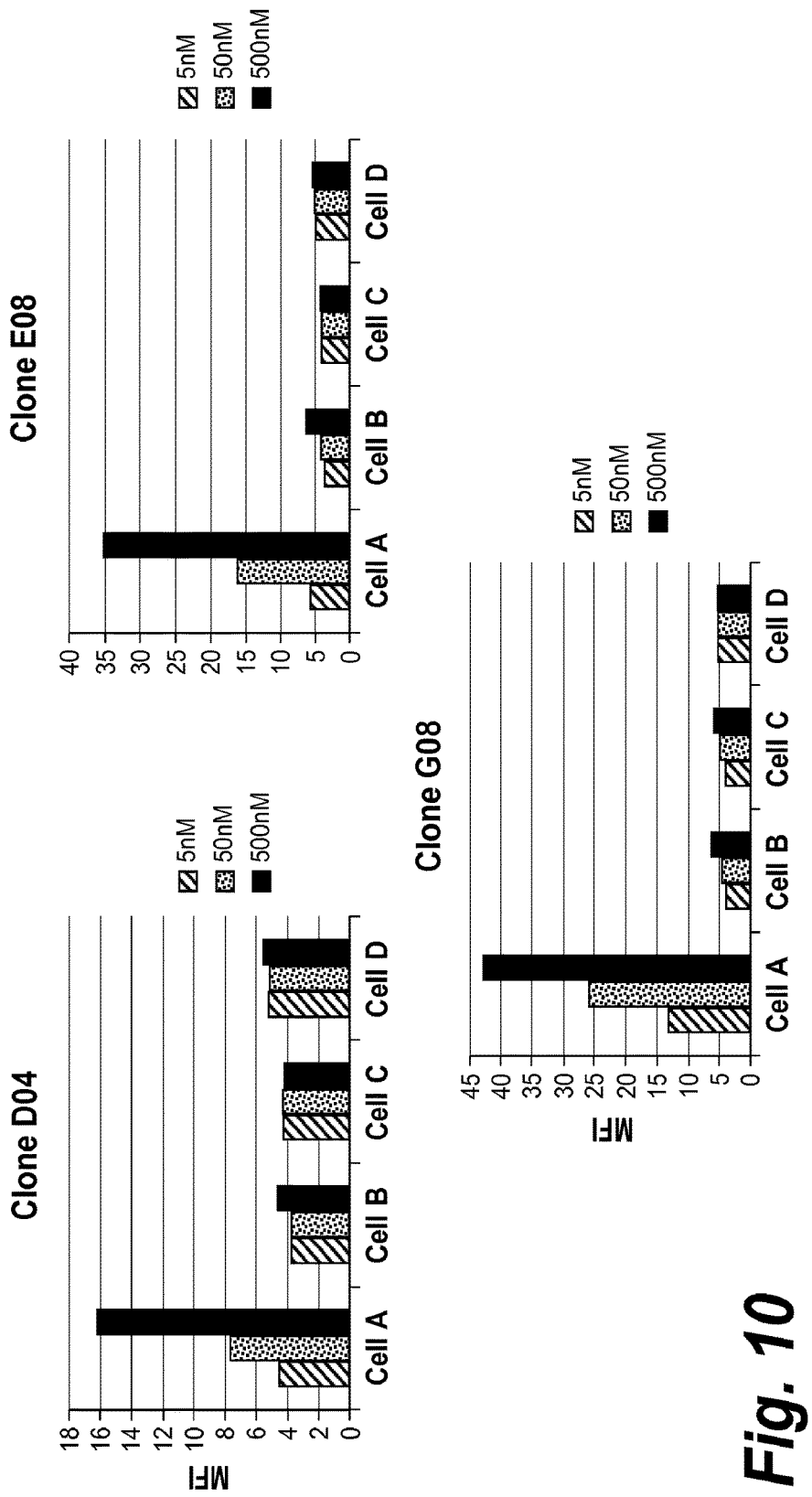
FIG. 10 depicts graphs showing the differential binding of VH molecules selected using the methods of the invention.

The binding pools and synthesized VHs were then subcloned into pET22b expression vectors. The VHs were produced in BL-21 *E. coli* cells and purified through C-terminal His tag using standard protocols. FACS assay was performed to assess the binding and selectivity of VHs to different cell types and the EC50 of the binders. High affinity and selective VH binders were identified through the live cell selection process (see FIGS. 8, 9 and 10).

We claim:

1. A method of identifying a binding polypeptide that specifically binds to a cell-surface antigen, the method comprising:
   (a) contacting a variegated nucleic acid-display library of binding polypeptides with a cell-surface antigen naturally expressed on an exterior surface of a first cell type, wherein the variegated nucleic acid-display library is a DNA-display library, wherein each member of the DNA-display library comprises a binding polypeptide linked through an intervening DNA linker to a DNA coding sequence encoding the binding polypeptide, and wherein the DNA linker comprises a restriction endonuclease site not present in the coding sequence of members of the DNA-display library;
   (b) washing unbound library members from the first cell type;
   (c) enzymatically separating bound library members from the first cell type by cleaving the restriction endonuclease site with a suitable restriction endonuclease; and
   (d) isolating from the library at least one library member that specifically binds to the cell-surface antigen on the exterior surface of the first cell type, thereby identifying a binding polypeptide that specifically binds to the cell surface antigen.

2. The method of claim 1, wherein prior to step (a), an unselected precursor of the variegated nucleic acid-display library of binding polypeptides is contacted with a second cell type that does not express the cell-surface antigen on its exterior surface, and library members that bind to the second cell type are isolated and removed from the unselected precursor of the variegated nucleic acid-display library to produce the variegated nucleic acid-display library used in step (a).

3. The method of claim 1, further comprising:
   (e) contacting the variegated nucleic acid-display library of binding polypeptides with a second cell type that does not express the cell-surface antigen, and isolating from the library at least one library member that specifically binds to the second cell type; and
   (f) selecting library members that specifically bind to the first cell type but not to the second cell type, thereby identifying a binding polypeptide that specifically binds to the cell-surface antigen.

4. The method of claim 1, wherein the method further comprises determining the DNA coding sequence of at least a portion of the isolated library members.

5. The method of claim 4, wherein the DNA coding sequence is determined by pyrosequencing.

6. The method of claim 1, where the antigen is a naturally occurring protein, glycan or lipid.

7. The method of claim 1, where the antigen is a glycophosphatidylinositol (GPI) anchored protein.

8. The method of claim 1, wherein the first cell type is a disease-associated variant of a normal cell.

9. The method of claim 1, wherein the first cell type is a tumor cell.

10. The method of claim 1, wherein the binding polypeptide is an antibody or fragment thereof.

11. The method of claim 1, wherein the binding polypeptide is an antibody VH or VL domain.

12. The method of claim 1, wherein the first cell type is a live cell.

13. The method of claim 3, wherein the first and second cell types are live cells.

* * * * *

SEQUENCE LISTING

<160> NUMBER OF SEQ ID NOS: 10

<210> SEQ ID NO 1
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 1
gatccctcga                                                          10

<210> SEQ ID NO 2
<211> LENGTH: 11
<212> TYPE: DNA
<213> ORGANISM: Artificial sequence

```
<220> FEATURE:
<223> OTHER INFORMATION: Synthetic oligonucleotide

<400> SEQUENCE: 2
cgcccggact c                                                        11

<210> SEQ ID NO 3
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 3
ttcccgatcc ga                                                       12

<210> SEQ ID NO 4
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 4
acgtgtctac c                                                        11

<210> SEQ ID NO 5
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 5
aacccaatcc c                                                        11

<210> SEQ ID NO 6
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 6
gacaccgggc cc                                                       12

<210> SEQ ID NO 7
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 7
ctactcctac c                                                        11

<210> SEQ ID NO 8
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 8
cctccttcga cc                                                       12
```

```
<210> SEQ ID NO 9
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 9
ccggctttcc aa                                                          12

<210> SEQ ID NO 10
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 10
cggcttcctg at                                                          12
```